United States Patent
Dijkstra et al.

(10) Patent No.: US 11,819,705 B2
(45) Date of Patent: Nov. 21, 2023

(54) WEARABLE DEVICE FOR BODY POSTURE DEVIATION DETECTION AND CORRECTION

(71) Applicant: LIGHT TREE, Amstelveen (NL)

(72) Inventors: Alain Dijkstra, Amstelveen (NL); Yvonne Johanna Margaretha Houthuijs, Amstelveen (NL)

(*) Notice: Subject to any disclaimer, the term of this patent is extended or adjusted under 35 U.S.C. 154(b) by 625 days.

(21) Appl. No.: 16/924,244

(22) Filed: Jul. 9, 2020

(65) Prior Publication Data
US 2021/0093879 A1 Apr. 1, 2021

(30) Foreign Application Priority Data
Oct. 1, 2019 (IN) .............................. 201911039655

(51) Int. Cl.
*A61N 2/00* (2006.01)
*A61B 5/11* (2006.01)
(Continued)

(52) U.S. Cl.
CPC ............ *A61N 2/002* (2013.01); *A61B 5/1116* (2013.01); *A61B 5/6812* (2013.01);
(Continued)

(58) Field of Classification Search
CPC .... A61N 2/002; A61N 5/1116; A61N 5/6812; A61N 5/6823; A61N 5/028;
(Continued)

(56) References Cited

U.S. PATENT DOCUMENTS 6,290,713 B1 * 9/2001 Russell ................ A61N 5/0616
607/91
7,476,557 B2 1/2009 Daniels et al.
(Continued)

FOREIGN PATENT DOCUMENTS

CN 208301772 U 1/2019
KR 200356267 Y1 7/2004
(Continued)

OTHER PUBLICATIONS

Lumo Lift https://www.lumobodytech.com/lumo-lift/.
(Continued)

*Primary Examiner* — Sunita Reddy
(74) *Attorney, Agent, or Firm* — Willie Jacques; Emanus, LLC

(57) ABSTRACT

A wearable device for detection of a posture deviation of a body of a user, and to provide proper alignment thereon, comprises a resting pad adapted to cover a back region of the body of the user, wherein the resting pad includes an internal surface oriented towards the back region, and an external surface oriented away from the back region, a supporting unit adapted to be attached with the resting pad, at the external surface, wherein the supporting unit further includes a back stretcher adapted to be deformed through flexure, and a flexing mechanism adapted to cause the flexure of the back stretcher and a sensor unit configured to determine deviation in the posture of the body of the user. Further, the resting pad is made of a flexible material to accommodate the flexure of the back stretcher.

19 Claims, 9 Drawing Sheets

(51) Int. Cl.
  *A61B 5/00* (2006.01)
  *A61F 5/02* (2006.01)
  *A61N 5/06* (2006.01)
  *A61N 2/02* (2006.01)
  *A61N 1/36* (2006.01)

(52) U.S. Cl.
  CPC ............ *A61B 5/6823* (2013.01); *A61F 5/028* (2013.01); *A61N 1/3604* (2017.08); *A61N 2/02* (2013.01); *A61N 5/0613* (2013.01); *A61B 2562/0219* (2013.01); *A61N 2005/0645* (2013.01); *A61N 2005/0652* (2013.01); *A61N 2005/0653* (2013.01); *A61N 2005/0659* (2013.01); *A61N 2005/0663* (2013.01)

(58) Field of Classification Search
  CPC ...... A61N 1/3604; A61N 2/02; A61N 5/0613; A61N 2562/0219; A61N 2005/0645; A61N 2005/0652; A61N 2005/0653; A61N 2005/0659; A61N 2005/0663; A61N 1/0456; A61N 1/0484; A61N 1/37282; A61N 2005/0662; A61B 5/4566; A61B 5/4836
  USPC ...................................................... 600/9–15
  See application file for complete search history.

(56) References Cited

U.S. PATENT DOCUMENTS

| | | | |
|---|---|---|---|
| 8,415,879 B2 | 4/2013 | Lowenthal et al. | |
| 8,809,126 B2 | 8/2014 | Lowenthal et al. | |
| 8,846,457 B2 | 9/2014 | Lowenthal et al. | |
| 8,852,467 B2 | 10/2014 | Lowenthal et al. | |
| 8,877,101 B2 | 11/2014 | Lowenthal et al. | |
| 9,018,833 B2 | 4/2015 | Lowenthal et al. | |
| 9,582,072 B2 | 2/2017 | Connor | |
| 2004/0039428 A1* | 2/2004 | Williams | A61N 5/0621 607/91 |
| 2005/0137462 A1* | 6/2005 | Cho | A47C 31/126 600/300 |
| 2007/0156208 A1* | 7/2007 | Havell | A61N 5/0616 607/88 |
| 2011/0301673 A1* | 12/2011 | Hoffer | A61N 5/0613 607/91 |
| 2013/0274839 A1* | 10/2013 | Johnson | A61N 5/06 607/90 |
| 2013/0317400 A1* | 11/2013 | Ferezy | A61N 1/0452 602/2 |
| 2014/0128942 A1* | 5/2014 | Bembridge | A61N 5/0613 607/90 |
| 2015/0182747 A1* | 7/2015 | Ajiki | A61N 1/37264 607/48 |
| 2015/0309563 A1* | 10/2015 | Connor | A61B 5/1071 73/865.4 |
| 2016/0140826 A1* | 5/2016 | Sahiholnasab | A61B 5/486 600/587 |
| 2016/0310064 A1* | 10/2016 | Cheng | A61B 5/1116 |
| 2016/0310065 A1* | 10/2016 | Arif | A61B 5/1116 |
| 2017/0216617 A1 | 8/2017 | Kariguddaiah | |
| 2017/0372582 A1* | 12/2017 | Qiao | A61B 5/7275 |
| 2018/0098732 A1* | 4/2018 | Williamson | G16H 80/00 |
| 2019/0117124 A1* | 4/2019 | Hsu | A61B 5/6892 |
| 2019/0240053 A1* | 8/2019 | Kazaryan | A61F 5/0111 |
| 2020/0268543 A1* | 8/2020 | Santaniello | A61F 5/028 |
| 2021/0077811 A1* | 3/2021 | Wong | A61N 1/36021 |
| 2022/0079795 A1* | 3/2022 | Gross | A61B 5/6812 |

FOREIGN PATENT DOCUMENTS

| | | |
|---|---|---|
| KR | 200395827 Y1 | 9/2005 |
| KR | 20130023864 A | 3/2013 |
| KR | 20190068842 A | 6/2019 |

OTHER PUBLICATIONS

Philips Blue Touch http://www.by-wire.net/philips-blue-touch/.
Bardsley, J. N. (2004), "International OLED Technology Roadmap", IEEE Journal of Selected Topics in Quantum Electronics, vol. 10, No. 1.

* cited by examiner

WEARABLE DEVICE FOR BODY POSTURE DEVIATION DETECTION AND CORRECTION

TECHNICAL FIELD

The subject matter of the present invention relates generally to posture correction devices. Particularly and not exclusively, the subject matter of the present invention relates to an enhanced device for human body posture correction thereby enabling the maintenance of good posture by causing the correct alignment of human body parts including spine and torso.

BACKGROUND ART

A proper and good posture for a person includes standing or sitting in the right position with the right alignment of body parts. It is a well-known fact that a good posture during any activity serves to maintain the physical fitness of the person, with additional health benefits including enhanced functioning of lungs, enhanced functioning of gastrointestinal system, proper and optimal functioning of spinal cord thereby reducing the risk of vertebral disk slipping and damage, overall improvement in the musculoskeletal system, and enhanced self-esteem. However, modern workforce requirements need people to carry out several functions at their work while sitting for long and extended hours. Due to the sedentary lifestyle and unawareness amongst the workforce of optimal and proper body posture, most of these working professionals do often suffer from several posture-related conditions including the development of back pain.

While there have been several solutions suggested in the art in the form of body posture correction devices, such solutions suffer from several drawbacks. One of the drawbacks of the body posture correction devices is that they are generally short term solutions and therefore are not capable of addressing chronic or repetitive posture-related conditions. This is because most of these devices are not easily or extensively customizable and do not account for the physiological attributes of a user, including age, gender, and other pre-existing conditions. Although, more recent solutions suggested in the art offer improvements to the conventional body posture correction devices, in a manner that the more recent solutions propose wearable devices made out of stretchable materials with adjustable constructions. However, the drawbacks associated with these devices lies in the fact that they are generally on a heavier side, which becomes a challenge in itself if they are to be worn for relatively long periods. As a consequence, contrary to their purpose, wearing these devices for sustained periods only exacerbates the existing posture-related conditions of the user. Further, ergonomically these devices have still not matured in terms of design. For example, improper tightening of their straps is liable to cause additional stress on the shoulders thereby causing additional discomfort to the user including reduced blood flow therein resulting in added pain in the shoulders. Besides, most of these devices require manual manipulation, and they generally lack in flexibility and adaptability.

Although attempts have been made to overcome the drawbacks related to the manual manipulation of the devices in the art by including several sensors in the proposed solutions, the sensors in such devices are configured to detect deviation from a predefined desired position of the human body and generate a signal (for example, in the form of haptic feedback or a sound alarm, etc.) in correlation with the deviation, thereby prompting the user to correct their position. However, issues related to customization, flexibility, and adaptability remain prevalent even with such solutions. Therefore, there is a need in the art for a posture correction device that does not suffer from the aforementioned deficiencies.

OBJECTS OF THE INVENTION

Some of the objects of the present invention are as follows:

It is an object of the present invention to provide a wearable, effective and reliable device for human body posture deviation detection and correction;

It is another object of the present invention to provide a wearable, effective and reliable device for human body posture deviation detection and correction that is lightweight;

It is yet another object of the present invention to provide a wearable, effective, and reliable device for human body posture deviation detection and correction that is relatively simple in construction and configuration;

It is an additional object of the present invention to provide a wearable, effective, and reliable device for human body posture deviation detection and correction that in addition to posture correction adopts electromagnetic irradiation for curative purposes for treating maladies such as slipped discs and chronic pain; and It is a further object of the present invention to provide a wearable, effective, and reliable device for human body posture deviation detection and correction that can be customized readily to account for user specific factors such as age, gender, and geography, etc.

Other objects, aspects, features, and goals of the present invention will be better understood from the following detailed description taken in conjunction with the accompanying drawings.

SUMMARY OF THE INVENTION

According to a first aspect of the present invention, there is provided a wearable device for detection of a posture deviation of a body of a user, and to provide proper alignment thereon, the wearable device comprising a resting pad adapted to cover a back region of the body of the user, wherein the resting pad includes an internal surface oriented towards the back region, and an external surface oriented away from the back region, a supporting unit adapted to be attached with the resting pad, at the external surface, wherein the supporting unit further includes a back stretcher adapted to be deformed through flexure, and a flexing mechanism adapted to cause the flexure of the back stretcher and a sensor unit configured to determine deviation in the posture of the body of the user. Also, the resting pad is made of a flexible material to accommodate the flexure of the back stretcher.

The flexing mechanism in combination with the sensor unit allows for the detection and correction of the deviation in the posture of the body of the user.

In one embodiment of the invention, the flexing mechanism includes a first main block and a second main block provided at a first main end and a second main end of the supporting unit, respectively, a first supporting block and a second supporting block provided at a first stretcher end and a second stretcher end of the back stretcher, respectively, a shaft provided between the first main block and the second main block and a movable block adapted to displace along the shaft through a displacement mechanism, wherein the first supporting block is attached with the first main block and the second supporting block is attached with the movable block, wherein, as a result, the displacement of the movable block along the shaft and towards the first main block is adapted to cause the flexure of the back stretcher.

The simplicity of the construction of the flexible mechanism and thus the overall wearable device makes the wearable device lightweight, capable of being made out of a wide variety of materials including synthetic polymers, and therefore relatively robust, sturdy while also being economical.

In one embodiment of the invention, the displacement mechanism is constituted by the shaft including external threads and the movable block including internal threads adapted to engage with the external threads of the shaft, wherein, as a result, rotation of the shaft causes the displacement of the movable block along the shaft.

In one embodiment of the invention, the displacement mechanism further comprises a rotatable assembly including a knob provided at one of the first main end and the second main end of the supporting unit and attached with the shaft, such that, the rotation of the knob causes the rotation of the shaft.

In one embodiment of the invention, the displacement mechanism further comprises an electrical motor provided at one of the first and the second ends of the supporting unit and attached with the shaft, wherein rotation of the electric motor causes the rotation of the shaft.

The inclusion of the electrical motor in the displacement mechanism in combination with the sensor unit allows for the automatic operation of the wearable device. The automatic operation makes the wearable device accessible to even unskilled users who may not be aware of the correct body positions during several different activities. The automatic operation also releases the users of the burden of always being in awareness of their body positions, thus allowing the users to concentrate on their day to day activities without unnecessary distractions.

In one embodiment of the invention, the wearable device further comprises a plurality of Light Emitting Diodes (LEDs) provided on the internal surface of the resting pad.

The LEDs have been known to have several therapeutic benefits, so while the construction and automatic operation of the wearable device would keep the user is a proper position, electromagnetic irradiation from LEDs may be used to treat any pre-existing conditions such as chronic pain in the vertebral column.

In one embodiment of the invention, the plurality of LEDs is adapted to emit electromagnetic radiation in red and infrared frequency ranges of the electromagnetic spectrum.

The red and infrared frequencies are known to offer several benefits such as reduction of muscle inflammation, skin repair, and enhanced blood flow.

In one embodiment of the invention, the sensor unit includes an Inertial Measurement Unit (IMU).

In one embodiment of the invention, the sensor unit is further configured to provide an indication in correlation with the determined deviation.

In one embodiment of the invention, the back stretcher is adapted to be provided over a lumbar region of the back region of the body of the user.

In one embodiment of the invention, the back stretcher is made from Acrylonitrile Butadiene Styrene (ABS) polymer.

In one embodiment of the invention, the wearable device further comprises a processor and a memory unit, the memory unit including machine-readable instructions that when executed by the processor, enables the processor to receive the determined deviation from the sensor unit and activate the flexing mechanism in correlation with the determined deviation.

In one embodiment of the invention, the processor is further configured to activate the flexing mechanism in response to a control input received from an electronic communication device.

In one embodiment of the invention, the wearable device further comprises a Pulsed Electromagnetic Field (PEMF) device adapted to provide PEMF therapy to the body of the user.

In one embodiment of the invention, the wearable device further comprises a Transcutaneous Electrical Nerve Stimulation (TENS) unit adapted to provide predefined stimulation to the back region of the body.

According to a second aspect of the present invention, there is provided a supporting unit adapted to be attached with a wearable device for detection of a posture deviation of a body of a user, and to provide proper alignment thereon, the supporting unit comprising a back stretcher adapted to be deformed through flexure, towards the wearable device and a flexing mechanism adapted to cause the flexure of the back stretcher. The flexing mechanism includes a first main block and a second main block provided at a first main end and a second main end of the supporting unit, respectively, a first supporting block and a second supporting block provided at a first stretcher end and a second stretcher end of the back stretcher, respectively, a shaft provided between the first main block and the second main block, a movable block adapted to displace along the shaft through a displacement mechanism, wherein the first supporting block is attached with the first main block and the second supporting block is attached with the movable block, wherein, as a result, the displacement of the movable block along the shaft and towards the first main block, is adapted to cause the flexure of the back stretcher.

In one embodiment of the invention, the displacement mechanism is constituted by the shaft including external threads and the movable block including internal threads adapted to engage with the external threads of the shaft, wherein, as a result, rotation of the shaft causes the displacement of the movable block along the shaft.

In one embodiment of the invention, the displacement mechanism further comprises a rotatable assembly including a knob provided at one of the first main end and the second main end of the supporting unit and attached with the shaft, such that, the rotation of the knob causes the rotation of the shaft.

In one embodiment of the invention, the displacement mechanism further comprises an electrical motor provided at one of the first and the second ends of the supporting unit and attached with the shaft, wherein rotation of the electric motor causes the rotation of the shaft.

According to a third aspect of the present invention, there is provided a method of utilizing a wearable device for detection of a posture deviation of a body of a user, and to provide proper alignment thereon, the wearable device comprising a resting pad adapted to cover a back region of the body of the user, the resting pad being constituted by a body region and a neck region, the resting pad further including an internal surface oriented towards and adapted to be in contact with the back region, and an external surface oriented away from the back region a supporting unit adapted to be attached with the resting pad, at the external surface, the supporting unit further including a back stretcher adapted to be deformed through flexure, towards the resting pad, wherein the resting pad is made of a flexible material to accommodate the flexure of the back stretcher, a first supporting block and a second supporting block provided at a first stretcher end and a second stretcher end of the back stretcher, respectively, a first main block and a second main block provided at a first main end and a second main end of the supporting unit, respectively, a shaft provided between the first main block and the second main block, a movable block adapted to displace along the shaft through a displacement mechanism, wherein the first supporting block is attached with the first main block and the second supporting block is attached with the movable block, wherein, as a result, the displacement of the movable block along the shaft and towards the first main block is adapted to cause the flexure of the back stretcher and a sensor unit configured to determine deviation in the posture of the body of the user, the sensor unit including an Inertial Measurement Unit (IMU). The method comprises steps of determining the deviation in the posture of the body of the user and in response to the determination of the deviation, displacing the movable block along the shaft, using the displacement mechanism, to cause the flexure of the back stretcher.

The following description is illustrative and is not intended to be in any way limiting. In addition to the illustrative aspects, embodiments, and features described above, further aspects, embodiments, and features will become apparent by reference to the following detailed description.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

DETAILED DESCRIPTION

Figure 1:
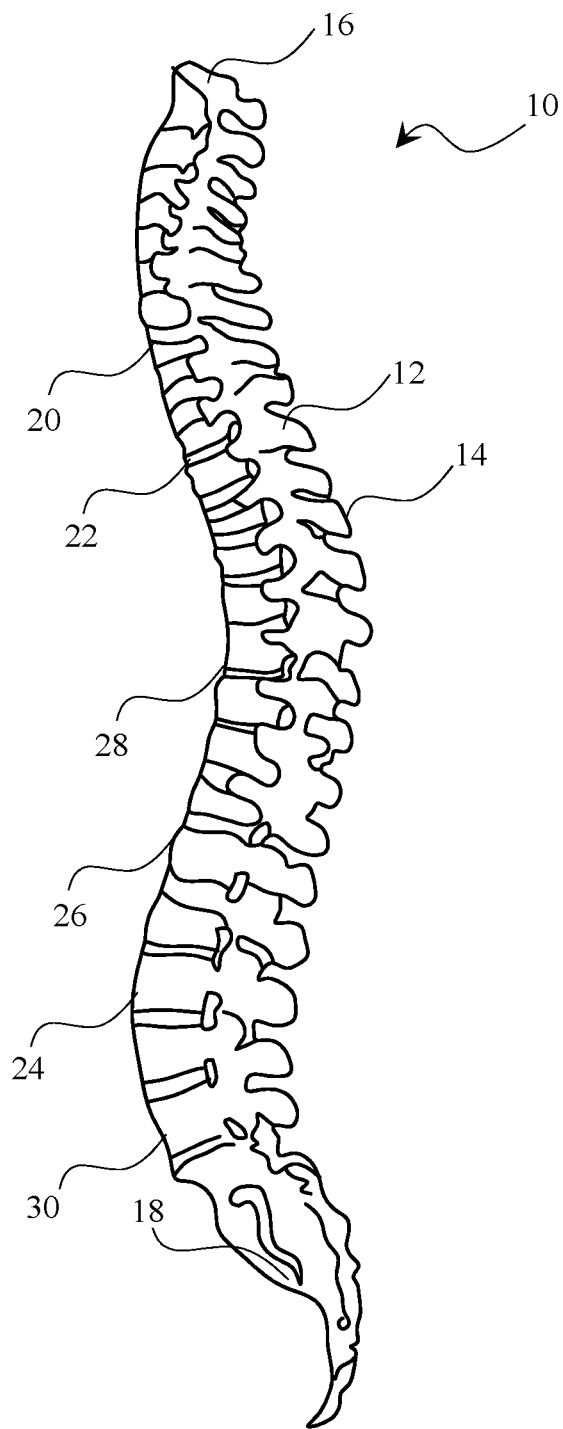
FIG. 1 illustrates a sectional view of a spinal column of an adult human being.

In order to ameliorate and overcome one or more drawbacks and disadvantages associated with the prior art and to provide additional advantages and improvements, a wearable device for human body posture deviation detection and correction is provided and illustrated herein in the form of a non-limiting and exemplary embodiment. Additional features and advantages are realized through the techniques of the disclosure of the present invention. Other embodiments and aspects of the disclosure of the present invention are described in detail herein and are considered a part of the claimed invention.

It is envisaged that a wearable device that allows a user to achieve proper posturing of the spinal column be provided. In that regard, the wearable device is envisaged to have a resting pad for covering the back region of the user. The resting pad is envisaged to support at least the neck and the torso of the user. Further, a supporting unit is envisaged to be attached to the resting pad that allows the user to achieve the intended proper posturing. Moreover, to determine deviation from the proper posture, a sensor unit has also been provided with the wearable device. The sensor unit may include one or more Inertial Measurement Units (IMU) that may be provided at one or more locations in the resting pad. Once the posture deviation has been determined, the supporting unit may be used to correct the posture and eliminate the deviation. In that regard, in an exemplary construction, the supporting unit may include a flexible member called a back stretcher provided between a fixed and a movable block. The movable block is envisaged to be able to displace along a shaft provided within the supporting unit. For example, if the sensor unit detects that the user is reclining more than that is recommended, the back stretcher in that regard may be flexed in the direction of the back region of the user, as the movable block is displaced towards the fixed block, thereby correcting the posture of the user by reducing the recline.

The displacement of the movable block along the shaft may be achieved through several mechanisms, such as a rotating screw, pulley and string or belt, and chain and sprocket, etc. Moreover, actuation for the displacement may either be provided manually, for example, through a knob or a handle or maybe through an electrical motor. Again, in case of the electrical motor being used for actuation, the actual operation may be operated by a user through an electrical switch or maybe automated by providing a microcontroller or a microprocessor operating in correlation with data aggregated by the sensor unit.

In an alternate construction of the supporting unit, several supporting elements capable of geometrically engaging with each other may be provided along two or more strings running along the back region of the user. The stings may be capable of rolling onto and be released from their respective spools on the provision of manual or automatic actuation. In that regard, on actuation of the spools in one rotational direction, the supporting elements may contract towards each other to cause tension in the string thereby applying sufficient pressure on the spinal column in case the spinal column has deviated beyond a threshold range. Alternately, on the actuation of the spools in an opposite rotation direction, the supporting elements may expand away from each other thereby releasing the tensioning in the strings and relaxing the spinal column of the user.

As additional features for enhancing the therapeutic value of the wearable device, several auxiliary systems may be provided with the wearable device. Such auxiliary systems may include Photo-Dynamic Therapy (PDT) with the use of red and infrared Light Emitting Diodes (LEDs), Pulsed Electromagnetic Field (PEMF) therapy and a Transcutaneous Electrical Nerve Stimulation (TENS) unit for providing therapeutic stimulation to the back region of the body. Referring to the figures now, the invention will be described in further detail.

FIG. 1 illustrates a sectional view of a spinal column of an adult human being. A well-developed human adult spinal column denoted by the reference numeral 10 consists of thirty-three (33) individual bones which are collectively known as vertebra denoted by the reference numeral 12. The vertebrae 12 are stacked one above the other forming a single continuous column-like structure denoted by the reference numeral 14. This linear vertical column 14 of vertebrae 12 provides mechanical support for the human being and further protects the human being from possible injuries to the spinal column 10.

The sectional view of the spinal column 10 illustrates a continuous curve beginning from the neck (which in medical terminology is known as 'cervical spine') denoted by the reference numeral 16 and ending with the triangular bottom portion (which in medical terminology is known as 'coccyx') denoted by the reference numeral 18. The curve 20 from the cervical spine 16 to thoracic spine denoted by the reference numeral 22 and the curve 24 from the lower spine (which in medical terminology is known as 'lumbar') denoted by the reference numeral 26 to the coccyx 18 are in the convex shape. The intermediate portion 28 beginning from thoracic spine 22 till lumbar 26 is concave in shape. The upper portion of the coccyx 18 is known as sacrum 30. These convex and concave shaped curve portions 20 and 24 of the spinal column 10 facilitate the enablement of a plurality of functioning of the human being including shock absorbance, maintenance of body balance, and the like.

Figure 2:
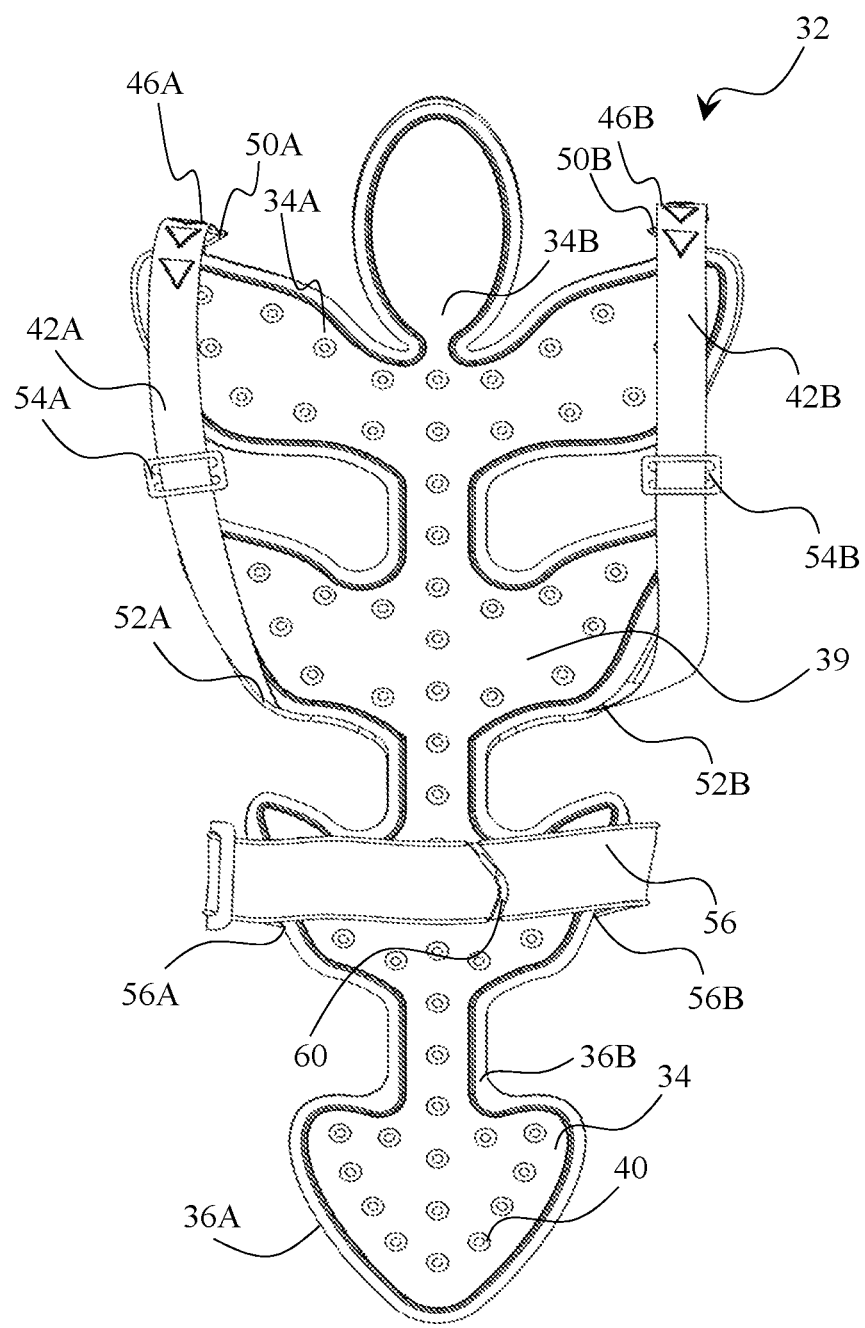
FIG. 2 illustrates a front view of a wearable device for the deviation detection and correction of the body posture of a user, in accordance with an embodiment of the present invention.

FIG. 2 illustrates a front view of a wearable device 32 for the deviation detection and correction of the body posture of a user, in accordance with an embodiment of the present invention. The wearable device 32 has a resting pad 34. The resting pad 34 is adapted to cover a back region of the body of the user. The resting pad 34 is constituted by a neck region 34B and a body region 34A. Moreover, the resting pad 34 includes an internal surface 36B and an external surface 36A. The internal surface 36B is oriented towards and adapted to be in contact with the back region of the user, and the external surface 36A is oriented away from the back region. It is further envisaged that the resting pad 34 is made of chemically stable and flexible material. The flexibility allows the resting pad 34 to conform to varying body shapes and form factors while chemical stability prevents the resting pad 34 from causing any skin irritations or allergic reactions in the body or on the surface of the skin.

A plurality of light sources preferably a plurality of Light Emitting Diodes [LEDs] 40 have been provided in the body region 34A, over the internal surface 36B, of the resting pad 34. The LEDs are characterized by their superior power efficiencies, smaller sizes, rapidity in switching, physical robustness, and longevity when compared with incandescent or fluorescent lamps In that regard, the plurality of LEDs 40 may be through-hole type LEDs (generally used to produce electromagnetic radiations of red, green, yellow, blue and white colors), Surface Mount LEDs, Bi-color LEDs, Pulse Width Modulated RGB (Red-Green-Blue) LEDs, and high power LEDs, etc. The LEDs have been known to have several therapeutic benefits, so while the construction and automatic operation of the wearable device 32 would keep the user is a proper position, electromagnetic irradiation from the plurality of LEDs 40 may be used to treat any pre-existing conditions such as chronic pain in the vertebral column Therefore, the plurality of LEDs 40 is envisaged to be oriented towards the back region, and therefore the electromagnetic radiation emitted from each one of the plurality of LEDs 40 would be incident upon the back region of the user.

Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGaInP) based compositions, while blue, green, and cyan use Indium Gallium Nitride based compositions. White light may be produced by mixing red, green, and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultra Violet (UV) LEDs may be combined with europium based phosphors to generate red and blue lights and copper and zinc doped zinc sulfide-based phosphor to generate green light.

In addition to conventional mineral-based LEDs, the plurality of LEDs 40 may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on generation of OLED panels can be found in Bardsley, J. N. (2004), *"International OLED Technology Roadmap", IEEE Journal of Selected Topics in Quantum Electronics*, Vol. 10, No. 1, that is included herein in its entirety, by reference. An exemplary description of flexible inorganic light-emitting diode strips can be found in granted U.S. Pat. No. 7,476,557B2, titled "Roll-to-roll fabricated light sheet and encapsulated semiconductor circuit devices", which is included herein in its entirety, by reference. In several embodiments, the plurality of LEDs 40 may also be micro-LEDs described through U.S. Pat. Nos. 8,809,126B2, 8,846, 457B2, 8,852,467B2, 8,415,879B2, 8,877,101B2, 9,018, 833B2, and their respective family members, assigned to NthDegree Technologies Worldwide Inc., which are included herein by reference, in their entirety. The plurality of LEDs 40, in that regard, may be provided as a printable composition of the micro-LEDs, printed on a substrate.

The electromagnetic radiation emitted by the plurality of LEDs 40 may be in the range of, however not limited to, red light frequencies or Infrared (IR) frequencies. The red and infrared frequencies are known to offer several benefits such as reduction of muscle inflammation, skin repair, and enhanced blood flow. The specific characteristics of the radiation emitted from the plurality of LEDs 40 may be variable depending upon the application. The specific characteristics in that regard may include mode of operation (pulsed or continuous), intensity, or amplitude, or wavelength or frequency, etc. The electromagnetic radiation from the plurality of LEDs 40 would also facilitate the relaxation of the muscles of the user.

Even though the construction of the wearable device 32 allows the wearable device 32 to be used for prolonged periods, it would still be advantageous to distribute even the minimal stress applied by the weight of the wearable device 32, over a relatively larger area. Therefore, there are also provided a pair of flexible and detachably attachable primary straps denoted by the reference numerals 42A and 42B respectively. The primary strap 42A is adapted to cover the right shoulder portion of the user and the primary strap 42B is adapted to cover the left shoulder portion of the user. Each one of the pair of the primary straps 42A and 42B is configured to extend respectively from the points 46A and 46B in the upper end of the body region 34A of the resting pad 34 of the wearable device 32 and terminate respectively at the points 52A and 52B. There are also provided adjustable buckles 54A and 54B each respectively for the pair of primary straps 42A and 42B for adjustable positioning of the wearable device 32 onto the back region of the user using the wearable device 32, allowing the wearable device 32 to be adaptable for varying heights of the upper portions or the torsos of several users.

Additionally, there is also provided one flexible and detachably attachable secondary strap 56 covering the middle torso region of the user. These primary straps 42A and 42B, and the secondary strap 56 are envisaged to be made of lightweight polymeric material. The secondary strap 56 is adapted to extend from the point 56A and terminate at the other point 56B of the resting pad 34. There is provided an arrangement of the loop and hook fasteners 60 for adjustable positioning of the wearable device 32 using the secondary strap 56, enabling the wearable device 32 to be adaptable for varying waste sizes of several users. The benefits associated with the loop and hook fasteners 60 include relatively stronger fastening hold with ease of application and release. Moreover, once worn out, the loop and hook fasteners 60 can be replaced with a replacement pair of fabric pieces including new loop and hook fasteners, with relative ease.

Figure 3:
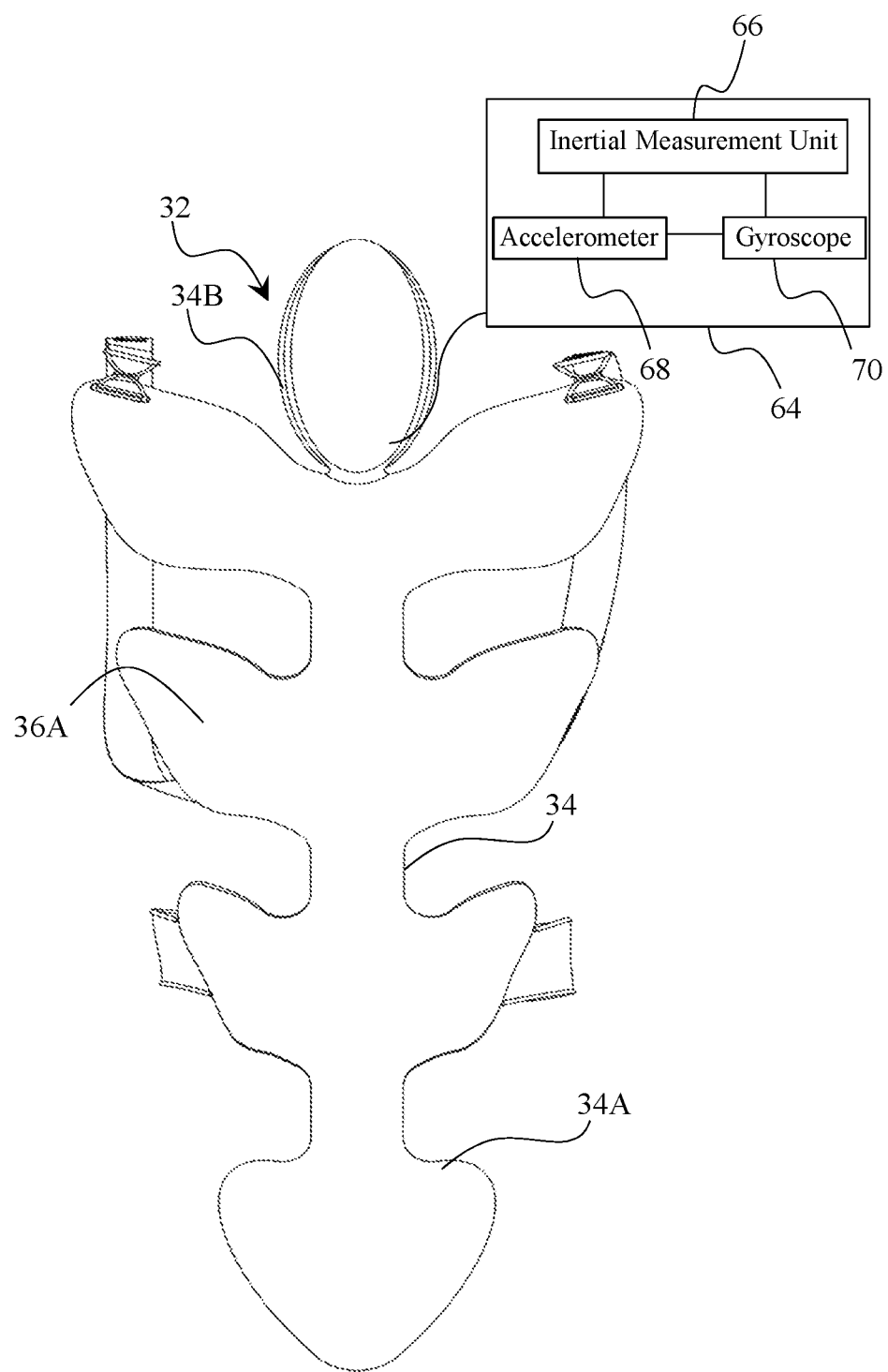
FIG. 3 illustrates a back view of the wearable device of FIG. 2.

FIG. 3 illustrates a back view of the wearable device 32 of FIG. 2. As illustrated, the wearable device 32 also includes a sensor unit 64. The sensor unit 64 is configured to automatically detect and identify the deformity or irregularity in the body posture of the user as soon as the user wears the wearable device 32. The presence of the sensor unit 64 releases the user of the responsibility to be constantly aware of their position to ensure they are not slouching or over-extending. This further allows the user to concentrate on the task at hand with which they may be involved with.

Preferably, the sensor unit 64 is positioned within the neck region 34B of the resting pad 34 of the wearable device 32, preferably in the lower portion of the neck region 34B of the resting pad 34 of the wearable device 32. The sensor unit 64 further includes an inertial measurement unit (IMU) 66. The inertial measurement unit (IMU) 66 is a sensor adapted to measure the angular rate and force. In a typical construction, the inertial measurement unit (IMU) 66 is composed of a three (3)-axis accelerometer 68 and a three (3)-axis gyroscope 70 thereby making the inertial measurement unit (IMU) 66 to be a six (6)-axis functional unit. The accelerometer 68 is an electromechanical device adapted to measure the linear deviation by which the body posture of the user has deviated from the standard position. The gyroscope 70 is a rotor that is adapted to measure the angular deviation by which the body posture of the user has deviated from the standard position.

The total deviation of the body posture is the total of the linear deviation and the angular deviation. For example, in a specific application, if total normalized deviation (i.e. by converting the linear deviation measured by the accelerometer 68 into a corresponding value of angular deviation, through a conversion function, and adding the converted angular deviation to the angular deviation measured by the gyroscope 70) is more than fifteen degrees (15°), then it is considered to be a deformity in the position and the posture of the user thereby identifying the body posture to be incorrect or improper body posture. The sensor unit 64 is adapted to notify the user of the deformity in at least one form. The form of notification of deformity may either be a light-based indication, or a sound-based indication, or a vibration-based indication or a character-based indication on an external digital electronic communication device or any combination thereof. Remedial embodiments for achieving correction in the posture of the user will be elucidated below.

Figure 4:
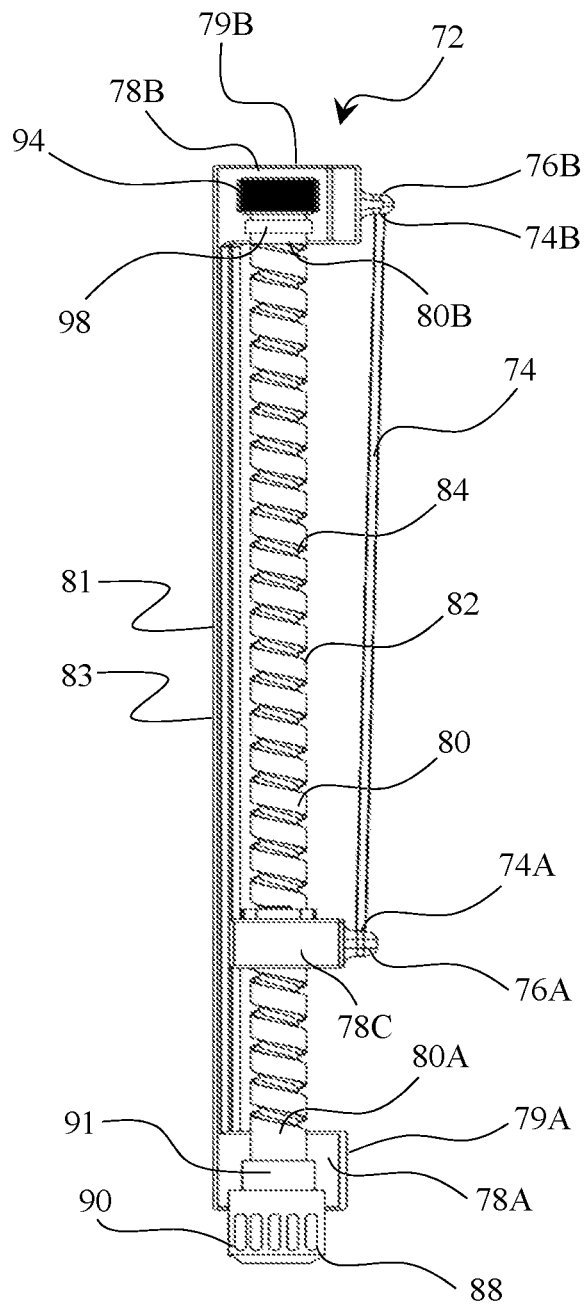
FIG. 4 illustrates a side view of a supporting unit of the wearable device, in accordance with an embodiment of the present invention.

FIG. 4 illustrates a side view of a supporting unit 72 of the wearable device 32, in accordance with an embodiment of the present invention. The supporting unit 72 is adapted to be attached with the resting pad 34 at the external surface 36A. The supporting unit 72 comprises a back stretcher 74 that can be made to attain the shape of an arched lumbar. In other words, the back stretcher 74 is adapted to be deformable through flexure. In that regard, the resting pad 34 is envisaged to be made of a flexible material to accommodate the flexure of the back stretcher 74. Further to this, the resting pad 34 is configured to possess sufficient flexibility to adapt to the minimum or maximum curvature of the back stretcher 74.

The back stretcher 74 is preferably made of Acrylonitrile Butadiene Styrene (ABS) which is an opaque thermoplastic and amorphous polymer. It can be heated to its melting point, cooled, and re-heated again without significant degradation. Further, the liquefaction of the thermoplastic of the back stretcher 74 allows it to be easily injection molded and then subsequently recycled. In several embodiments of the present invention, the back stretcher 74 is adapted to be provided over a lumbar region of the back region of the body of the user.

The supporting unit 72 further includes a flexing mechanism 81 adapted to cause the flexure of the back stretcher 74. The flexing mechanism 81 includes a first supporting block 76A and a second supporting block 76B provided at a first stretcher end 74A and a second stretcher end 74B, respectively, of the back stretcher 74. The first stretcher end 74A of the back stretcher 74 is fixed to the first supporting block 76A and the second stretcher end 74B of the back stretcher 74 is fixed to the second supporting block 76B.

There are also provided a first main block 78A and a second main block 78B provided at a first main end 79A and a second main end 79B of the supporting unit 72. Between the first 78A and the second 78B main blocks, there is provided a shaft 80. The shaft 80 is configured to extend from the interior of the first main block 78A till the interior of the second main block 78B. Between the first 78A and the second 78B main blocks, and along the length of the shaft 80, there is provided a movable block 78C. The movable block 78C receives and is attached to the second supporting block 76B. The movable block 78C is adapted to displace along the shaft 80 through a displacement mechanism 83. The displacement of the movable block 78C along the shaft 80 and towards the first main block 78A is adapted to cause the flexure of the back stretcher 74.

In order to further elaborate on the displacement mechanism 83, it is envisaged that the tolerance of the movable block 78C is identical to the tolerance of the shaft 80. Further, in one embodiment of the invention, the displacement mechanism 83 is constituted by the shaft 80 including external threads and the movable block 78C including internal threads adapted to engage with the external threads of the shaft 80. Therefore, the rotation of the shaft 80 causes the displacement of the movable block 78C along the shaft 80. For example, the external threads of the shaft 80 and the internal threads of the movable block 78C may include helical thread 82 having a fixed pitch 84. The internal helical thread and pitch (not shown in the drawings of FIG. 4 and FIG. 5) of the movable block 78C are configured in such a way as to facilitate its motion both in the downward direction as well as in the upward direction along the length of the shaft 80. However, a person skilled in the art would appreciate that the displacement mechanism 83 is not limited to the illustrated screw-based mechanism. Several alternate arrangements of the displacement mechanism 83 are possible without departing from the scope of the invention, including, but not limited to, those based on belt/string/cable and pulleys, chain and sprocket, and rack and pinion gears, etc.

Also, it is illustrated in FIG. 4, there is provided a knob 88 at the first main end 79A of the first main block 78A. Alternately, the knob 88 may also be provided at the second main end 79B of the second main block 78B. The knob 88 has a knob head 90 and a knob shaft 91. The knob shaft 91 of the knob 88 is adapted to receive an end 80A of the shaft 80. The knob shaft 91 is operably coupled to the shaft 80. The rotational axis of the knob 88 is coinciding with the rotational axis of the shaft 80 to make co-axial alignment in such a way that the rotation of the knob 88 causes the rotation of the shaft 80.

Figure 5:
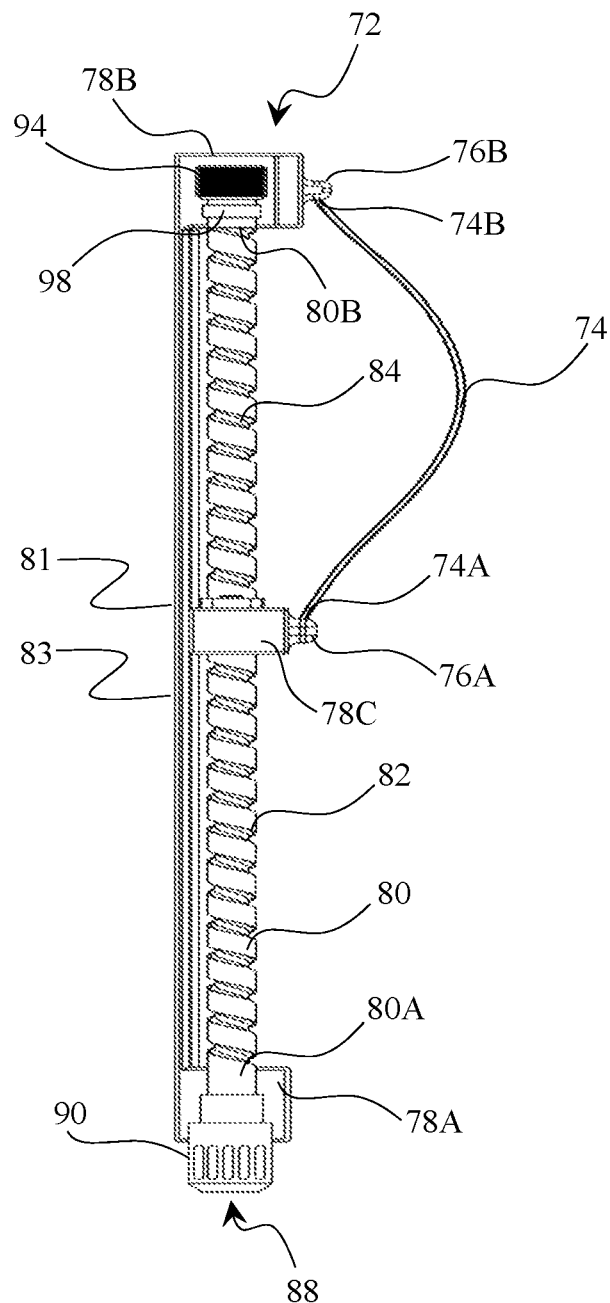
FIG. 5 illustrates a second configuration of the supporting unit of FIG. 4.

FIG. 5 illustrates a second configuration of the supporting unit of FIG. 4. The manual clock-wise or the counter-clockwise rotation of the knob 88 using the knob head 90 causes the rotation of the knob shaft 91 which in turn causes the clockwise or the counter-clockwise rotation of the shaft 80. Now, the counterclockwise rotation of shaft 80 causes the linear motion of the movable block 78C away from the first main block 78A. This shift of position of the movable block 78C away from the first main block 78A causes the increase in curvature of the back stretcher 74.

The maximum curvature of the back stretcher 74 is suitable and advisable for a person having a maximum deviation of the body posture. On the other hand, the clockwise rotation of the shaft 80 causes the linear motion of the movable block 78C towards the first main block 78A. The shift of position of the movable block 78C towards the first main block 78A causes the decrease in curvature of the back stretcher 74. At the maximum elongation of the stretcher 74, the person wearing the wearable device 32 feels complete relaxation. The knob operated functioning of the supporting unit 72 is a mechanical operation wherein the user using the wearable device 32 is required to adjustably position the wearable device 32 using his hand for rotating the knob head 90.

To make the automated functioning of the supporting unit 72 and in turn, the automated functioning of the wearable device 32, the other end 80B of the shaft 80 is fixed with an electrical motor 94 as shown in FIGS. 4 and 5. The electrical motor 94 may be a Direct Current (D.C.) motor, for example, a stepper motor or a servo motor provided at the second end 79B of the supporting unit 72. In that regard, a motor shaft (Not shown) is functionally and/or structurally coupled to the shaft 80 using a coupler 98. The inclusion of the electrical motor 94 in the displacement mechanism 83 in combination with the sensor unit 64 allows for the automatic operation of the wearable device 32. The automatic operation makes the wearable device 32 accessible to even unskilled users who may not be aware of the correct body positions during several different activities.

Figure 6:
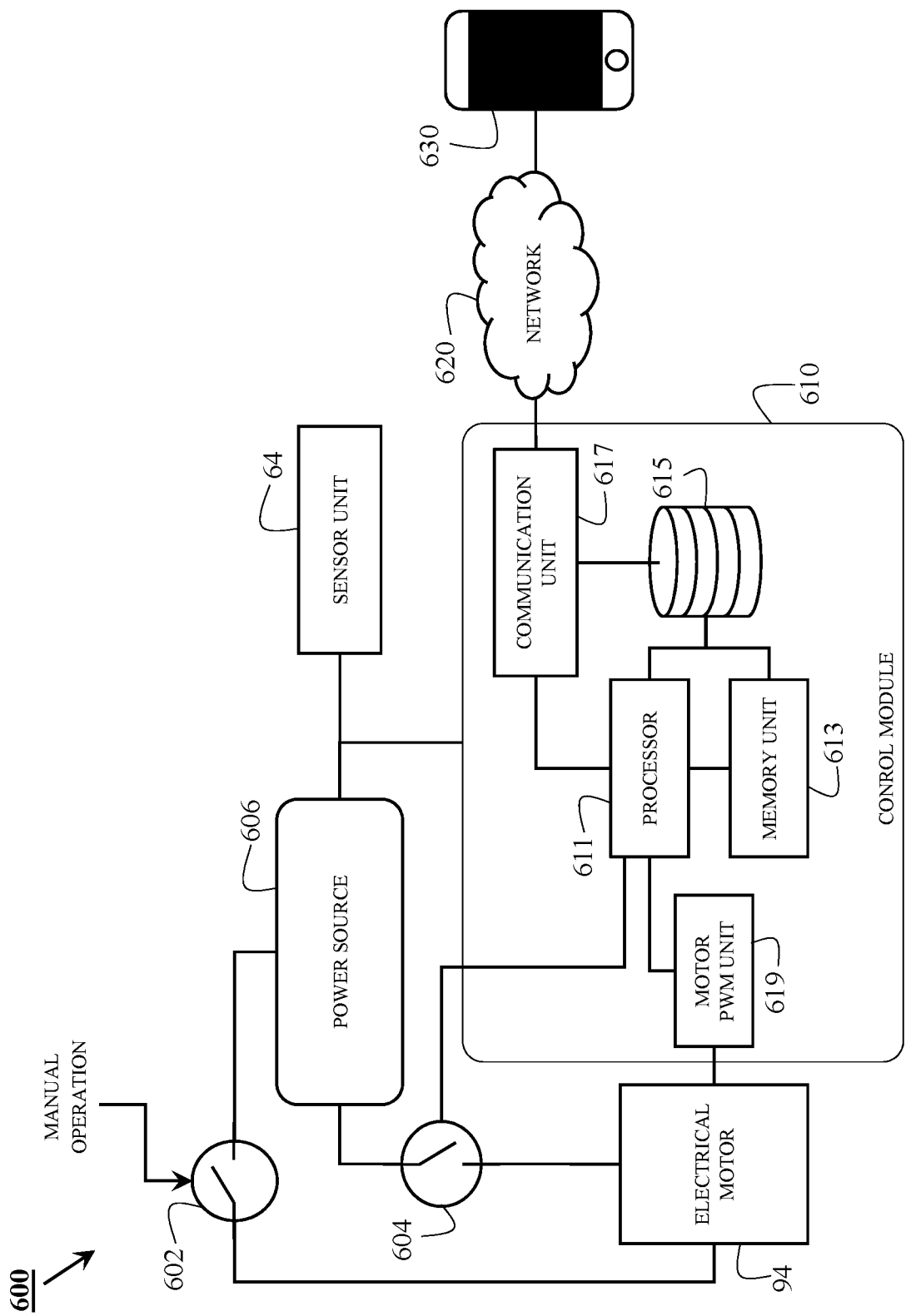
FIG. 6 illustrates a logical diagram of a control architecture for the wearable device, in accordance with an embodiment of the present invention.

FIG. 6 illustrates a logical diagram of a control architecture 600 for the wearable device 32, in accordance with an embodiment of the present invention. The control architecture 600 includes a manual switch 602 and a processor operated switch 604 connecting the electrical motor 94 with a power source 606. The power source 606 may be a rechargeable or a replaceable battery, such as Lithium-based or Nickel Metal Hydride based batteries. During manual operation of the wearable device 32, the user may allow electrical power to be provided directly to the electrical motor 94 by operating on the manual switch 602. However, in the automated functioning of the wearable device 32, the wearable device 32 includes a control module 610 including a processor 611, such as a microprocessor, a microcontroller, a general-purpose processor, a Field Programmable Gate Array (FPGA) or an Application Specific Integrated Circuit (ASIC), that may control the operation of the electrical motor 94 through the processor operated switch 604. In that regard, the processor operated switch 604 may be an electromechanical switch such as a relay or a solid-state switch such as a transistor.

The clock-wise (or the counter-clockwise) rotation of the electrical motor 94 causes the clock-wise or the counter-clockwise rotation of the motor shaft which in turn causes the clockwise (or the counter-clockwise) rotation of the shaft 80. Now, the counter-clockwise rotation of shaft 80 causes the linear motion of the movable block 78C to move towards the first main block 78A. This shift of position of the movable block 78C towards the first main block 78A causes the decrease in curvature of the back stretcher 74. The minimum curvature of the back stretcher 74 is suitable and advisable for a person having a minimum deviation of the body posture. At the minimum curvature or maximum elongation of the stretcher 74, the person wearing the wearable device 32 feels complete relaxation. On the other hand, the clockwise rotation of the shaft 80 causes the linear motion of the movable block 78C to move away from the first main block 78A. The shift of position of the movable block 78C away from the first main block 78A causes the increase in curvature of the back stretcher 74.

In addition, the processor 611 may also control motor characteristics such as speed, torque, and angle of rotation through a motor Pulse Width Modulation (PWM) unit 619 provided within the control module 610 in response to data received from the sensor unit 64. Control logic for operation and control of the wearable device 32 may be provided in the form of machine-readable instructions provided in a memory unit 613. The memory unit 613 is envisaged to be a volatile memory unit. Further, any data received or generated may be stored in a non-volatile storage unit 615. The processor 611, however, may also operate the electrical motor 94 on receiving a control signal from an external digital electronic communication device 630 that may be either a cell phone, or a laptop computer, or a tablet computer, or a notebook computer, or an iPhone, or an iPod, or an iPad. The electronic communication between the external digital electronic communication device 630 associated with the user and the wearable device 32 may be a wireless communication through a network 620. The network 620 used in the wireless communication may either be Bluetooth, or wireless-fidelity (Wi-Fi), or near field communication (NFC), or ZigBee, or Z-Wave, or an internet protocol (IP) version 6 low-power wireless personal area network (6LoWPAN).

Figure 7:
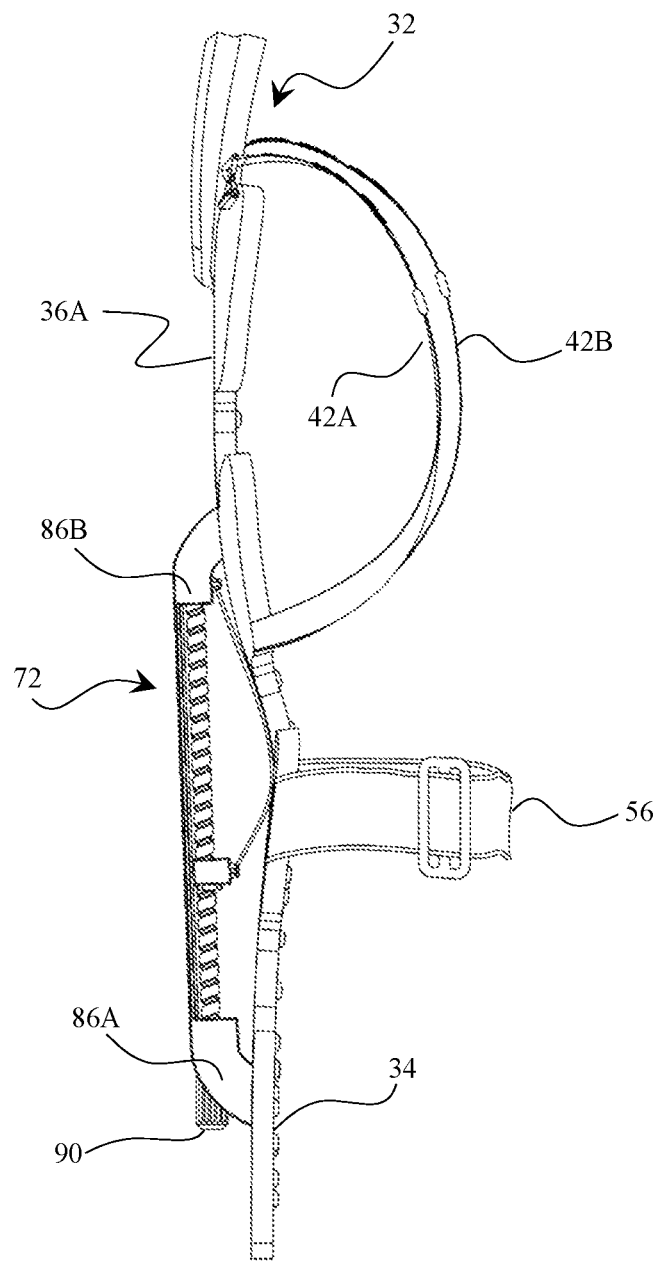
FIG. 7 illustrates an assembly of the supporting unit of FIG. 5, with a resting pad of the wearable device, in accordance with an embodiment of the present invention.

FIG. 7 illustrates an assembly of the supporting unit 72 of FIG. 5, with the resting pad 34 of the wearable device 32, in accordance with an embodiment of the present invention, illustrating the maximum curvature of the back stretcher 74. The knob 88 is adapted for manually operating the supporting unit 72. The electrical motor 94 is adapted for electro-mechanical operation of the supporting unit 72. The two fixing means 86A and 86B respectively enclose the first 78A and the second 78B main blocks. Further to this, each of these fixing means 86A and 86B is adapted to operably fix the supporting unit 72 to the external surface 36A of the body region 34A of the resting pad 34 of the wearable device 32.

The material of the first 76A and the second 76B supporting blocks, the first 78A and the second 78B main blocks, the movable block 78C, the shaft 80, the fixing means 86A and 86B and the knob 88 may be High-Density Polyethylene (HDPE) which is a thermoplastic polymer made from ethylene as starting constituent. The HDPE is a light-weight durable material exhibiting the property of malleability thereby facilitating the molding molded into nearly any shape. Further, HDPE is impact resistant, long-lasting, and weather resistant. Furthermore, HDPE resists mold, mildew, rotting, and insects.

The construction of the supporting unit 72, however, is not limited to the embodiments described above. The purpose of the supporting unit 72 is to generate enough tension or compression to maintain the proper posture of the user, as intended through this invention. The following discussion elucidates another alternative embodiment of the wearable device 32 that has been provided with the supporting unit 72 that has a construction that is different from the construction described above. While the following embodiments of the wearable device 32 may or may not fall within the scope of the appended claims, the applicant intends to reserve the right of claiming the following embodiments in a later related application, claiming priority, at least in part, from the instant application.

Figure 8:
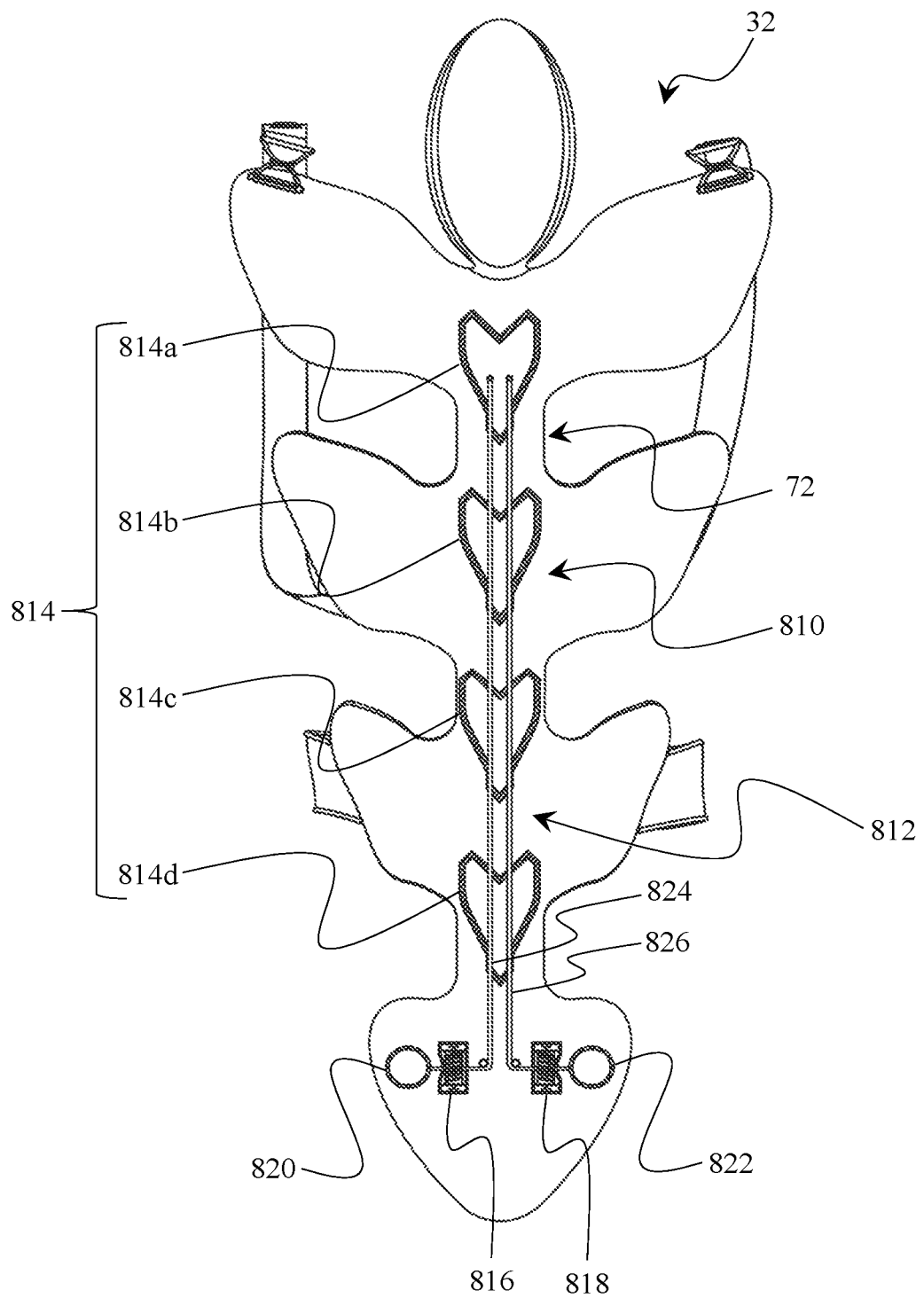
FIG. 8 illustrates a back view of the wearable device in accordance with an alternative embodiment of the present invention.
Figure 9:
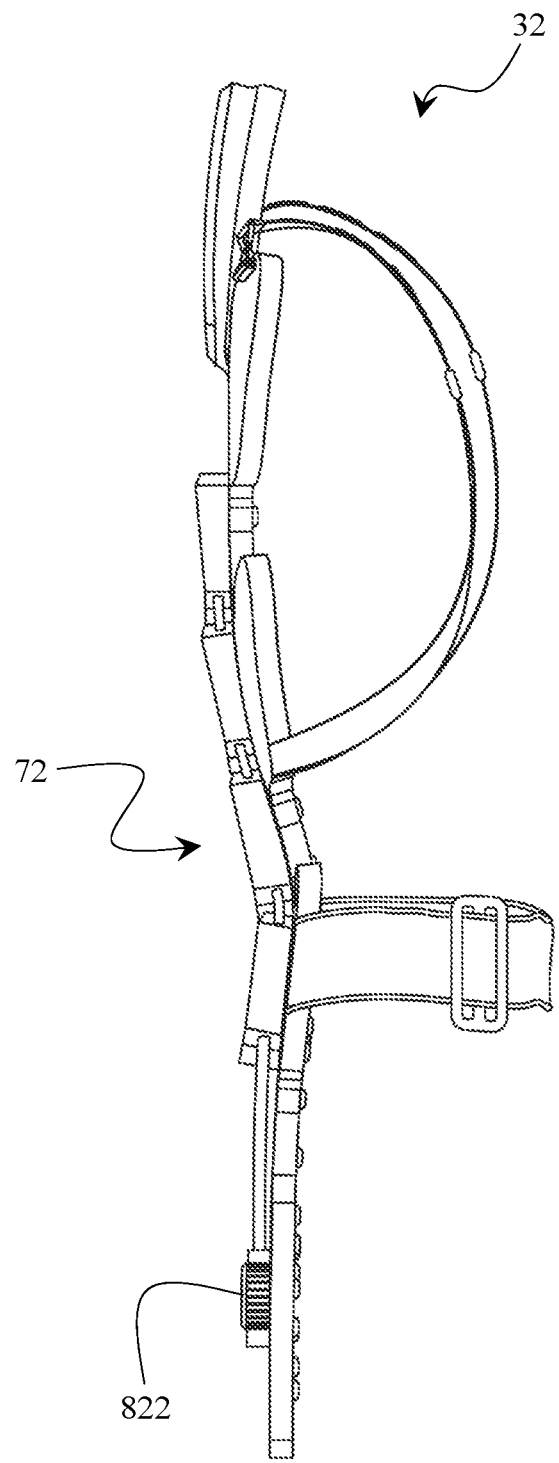
FIG. 9 illustrates a side view of the wearable device of FIG. 8.

FIG. 8 illustrates a back view of the wearable device 32, in accordance with an alternative embodiment of the present invention. FIG. 9 illustrates a side view of the wearable device of FIG. 8. As illustrated in FIGS. 8 and 9, the supporting unit 72 includes a metallic supporting frame 810 for providing mechanical support to the back portion of the upper torso region of the user. The metallic supporting frame 810 includes a vertical column 812 of a plurality of supporting elements 814 (for example 814a, 814b, 814c, and 814d) providing the required mechanical support. The length of the vertical column 812 extends from the upper end to the lower tip of the body region thereby covering the length of the spinal column of the user. There are also provided a pair of spools 816 and 818 wherein each spool is positioned on either side of the lower tip of the body region of the supporting unit 72. A pair of strings 824, 826 are also provided with each string extending from one of the pair of spools 816 and 818 and passing through each one of the plurality of supporting elements 814.

In operation, through the rotation of the pair of spools 816 and 818, either individually or in combination, in one direction causes the contraction of the plurality of supporting elements 814 towards each other and the rotation of the pair of spools 816 and 818, either individually or in combination, in an opposite direction causes the expansion of the plurality of supporting elements 814 away from each other. The rotation of the pair of spools 816 and 818, may be achieved through a pair of actuating mechanisms 820 and 822, respectively. The pair of actuation mechanisms 820 and 822 may be embodied as individual knobs or motors or may be embodied as a combined mechanism being driven by an individual motor. The contraction and expansion of the plurality of supporting elements 814 facilitate the stable fixing of the wearable device 32 on to the back portion of the user. Moreover, the rotation of the pair of spools 816 and 818 may either be achieved manually or maybe an automated rotation. The automated rotation again may include rotating the pair of spools 816 and 818 with the help of a stepper or a servo motor that can be actuated and controlled using an external digital electronic communication device associated with the user wearing the wearable device 32. The main functional element in the supporting unit 72, of the alternative embodiment of the wearable device 32 as illustrated in FIG. 8 and FIG. 9 is the vertical column 812 of the plurality of supporting elements 814, and any combination thereof. It is to be noted here that any of the aforementioned elements, such as the strings 824 and 826, the spools 816 and 818, and the plurality of supporting elements, of the embodiments discussed through FIG. 8 and FIG. 9 may be made from a plastic material, a metal or an alloy or a composite material, etc., depending upon specific application requirements such as weight, cost, manufacturability, and available technology, etc.

Additionally, in several alternate embodiments of the present invention, a Pulsed Electromagnetic Field (PEMF) therapy device can also be included. The PEMF device is preferably included embedded in the mid-portion between the resting pad 34 and the supporting unit 72. In its simple construction, the pulsed electromagnetic field (PEMF) device consists of a plurality of a finite number of flat spiral coils to produce an even electromagnetic field. Then, a frequency generator is used to energize the coils to create a pulsed electromagnetic field. The PEMF therapy device is adapted in the invention to provide effective electromagnetic stimulation of the spinal cord as an alternative remedy for chronic spinal pain. Additionally, the wearable device 32 further includes a Transcutaneous Electrical Nerve Stimulation (TENS) unit for providing suitable and required stimulation to the back portion of the user using the device.

From the foregoing description, it will be seen that the instant invention is well adapted to achieve all ends and objects hereinabove set forth together with other advantages which are obvious and which are inherent to the structure.

Technical Advantages and Economic Significance of the Present Invention

The present invention provides a wearable device for body posture deviation detection and correction. The wearable device as disclosed in the description is a light-weight wearable device that provides an effective and reliable way for human body posture deviation detection and correction. Further, the device adapts light energy additionally to provide a therapeutic effect to the back region of the user for applications such as skin treatment, pain relief, and muscle relaxation. The device can be worn by anyone irrespective of age, gender, and geography.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to be providing the broadest scope consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A wearable device for detection of a posture deviation of a body of a user, and to provide proper alignment thereon, the wearable device comprising:

a resting pad configured to cover a back region of the body of the user, wherein the resting pad includes an internal surface oriented towards the back region, and an external surface oriented away from the back region;

a supporting unit configured to be attached with the resting pad at the external surface, wherein the supporting unit further includes a back stretcher configured to be deformed through flexure, and a flexing mechanism configured to cause the flexure of the back stretcher; and a sensor unit configured to determine deviation from the proper alignment in the posture of the body of the user, wherein the resting pad is made of a flexible material to accommodate the flexure of the back stretcher, wherein the flexing mechanism comprises:
  a first main block and a second main block provided at a first main end and a second main end of the supporting unit, respectively,
  a first supporting block and a second supporting block provided at a first stretcher end and a second stretcher end of the back stretcher, respectively,
  a shaft provided between the first main block and the second main block, and
  a movable block configured to displace along the shaft through a displacement mechanism, wherein the first supporting block is attached with the first main block and the second supporting block is attached with the movable block in a manner that the displacement of the movable block along the shaft and towards the first main block is configured to cause the flexure of the back stretcher,
  wherein the flexure of the back stretcher due to the displacement of the movable block is configured to correct the deviation determined by the sensor unit to provide the proper alignment of the posture of the body of the user.

2. The wearable device as claimed in claim 1, wherein the displacement mechanism is constituted by the shaft including external threads and the movable block including internal threads configured to engage with the external threads of the shaft in a manner that rotation of the shaft causes the displacement of the movable block along the shaft.

3. The wearable device as claimed in claim 2, wherein the displacement mechanism further comprises a rotatable assembly including a knob provided at one of the first main end and the second main end of the supporting unit and attached with the shaft, such that, the rotation of the knob causes the rotation of the shaft.

4. The wearable device as claimed in claim 2, wherein the displacement mechanism further comprises an electrical motor provided at one of the first and the second ends of the supporting unit and attached with the shaft, wherein rotation of the electric motor causes the rotation of the shaft.

5. The wearable device as claimed in claim 1, further comprising a plurality of Light Emitting Diodes (LEDs) provided on the internal surface of the resting pad.

6. The wearable device as claimed in claim 5, wherein the plurality of LEDs are configured to emit electromagnetic radiation in red and infrared frequency ranges of the electromagnetic spectrum.

7. The wearable device as claimed in claim 1, wherein the sensor unit includes an Inertial Measurement Unit (IMU).

8. The wearable device as claimed in claim 1, wherein the sensor unit is further configured to provide an indication in correlation with the determined deviation.

9. The wearable device as claimed in claim 1, wherein the back stretcher is configured to be provided over a lumbar region of the back region of the body of the user.

10. The wearable device as claimed in claim 1, wherein the back stretcher is made from Acrylonitrile Butadiene Styrene (ABS) polymer.

11. The wearable device as claimed in claim 1, further comprising a processor and a memory unit, the memory unit including machine-readable instructions that when executed by the processor, enables the processor to:
  receive the determined deviation from the sensor unit; and
  activate the flexing mechanism in correlation with the determined deviation.

12. The wearable device as claimed in claim 11, wherein the processor is further configured to activate the flexing mechanism based on a control input received from an electronic communication device.

13. The wearable device as claimed in claim 1, further comprising a Pulsed Electromagnetic Field (PEMF) device adapted to provide PEMF therapy to the body of the user.

14. The wearable device as claimed in claim 1, further comprising a Transcutaneous Electrical Nerve Stimulation (TENS) unit adapted to provide predefined stimulation to the back region of the body.

15. A supporting unit configured to be attached with a wearable device for detection of a posture deviation of a body of a user, and to provide proper alignment thereon, the supporting unit comprising:
  a back stretcher configured to be deformed through flexure, towards the wearable device; and
  a flexing mechanism configured to cause the flexure of the back stretcher; wherein the flexing mechanism includes:
  a first main block and a second main block provided at a first main end and a second main end of the supporting unit, respectively;
  a first supporting block and a second supporting block provided at a first stretcher end and a second stretcher end of the back stretcher, respectively;
  a shaft provided between the first main block and the second main block;
  a movable block configured to displace along the shaft through a displacement mechanism, wherein the first supporting block is attached with the first main block and the second supporting block is attached with the movable block in a manner that the displacement of the movable block along the shaft and towards the first main block, is configured to cause the flexure of the back stretcher,
  wherein the flexure of the back stretcher due to the displacement of the movable block is configured to correct the detected posture deviation of the body of the user to provide the proper alignment of the posture of the body of the user.

16. The wearable device as claimed in claim 15, wherein the displacement mechanism is constituted by the shaft including external threads and the movable block including internal threads configured to engage with the external threads of the shaft in a manner that rotation of the shaft causes the displacement of the movable block along the shaft.

17. The wearable device as claimed in claim 16, wherein the displacement mechanism further comprises a rotatable assembly including a knob provided at one of the first main end and the second main end of the supporting unit and attached with the shaft, such that, the rotation of the knob causes the rotation of the shaft.

18. The wearable device as claimed in claim 16, wherein the displacement mechanism further comprises an electrical motor provided at one of the first and the second ends of the supporting unit and attached with the shaft, wherein rotation of the electric motor causes the rotation of the shaft.

19. A method of utilizing a wearable device for detection of a posture deviation of a body of a user, and to provide proper alignment thereon, the wearable device comprising:
- a resting pad configured to cover a back region of the body of the user, the resting pad being constituted by a body region and a neck region, the resting pad further including an internal surface oriented towards and configured to be in contact with the back region, and an external surface oriented away from the back region;
- a supporting unit configured to be attached with the resting pad, at the external surface, the supporting unit further including:
  - a back stretcher configured to be deformed through flexure, towards the resting pad, wherein the resting pad is made of a flexible material to accommodate the flexure of the back stretcher,
  - a first supporting block and a second supporting block provided at a first stretcher end and a second stretcher end of the back stretcher, respectively,
  - a first main block and a second main block provided at a first main end and a second main end of the supporting unit, respectively,
  - a shaft provided between the first main block and the second main block, a movable block configured to displace along the shaft through a displacement mechanism, wherein the first supporting block is attached with the first main block and the second supporting block is attached with the movable block in a manner that the displacement of the movable block along the shaft and towards the first main block is configured to cause the flexure of the back stretcher; and
- a sensor unit configured to determine deviation in the posture of the body of the user, the sensor unit including an Inertial Measurement Unit (IMU);

the method comprising steps of:
- determining the deviation in the posture of the body of the user via the sensor unit; and
- based on the determination of the deviation, displacing the movable block along the shaft, using the displacement mechanism, to cause the flexure of the back stretcher,
- wherein the flexure of the back stretcher due to the displacement of the movable block is configured to correct the deviation determined by the sensor unit to provide the proper alignment of the posture of the body of the user.

* * * * *